(12) United States Patent
Spano

(10) Patent No.: US 8,857,428 B2
(45) Date of Patent: Oct. 14, 2014

(54) DILATED NASAL SLEEP MASK

(76) Inventor: Michael J. Spano, New York, NY (US)

( * ) Notice: Subject to any disclaimer, the term of this patent is extended or adjusted under 35 U.S.C. 154(b) by 618 days.

(21) Appl. No.: 12/976,600

(22) Filed: Dec. 22, 2010

(65) Prior Publication Data

US 2012/0160240 A1    Jun. 28, 2012

(51) Int. Cl.
*A61M 15/00* (2006.01)
*A61F 5/08* (2006.01)
*A61F 9/04* (2006.01)

(52) U.S. Cl.
CPC .... *A61F 5/08* (2013.01); *A61F 9/04* (2013.01)
USPC .................. 128/202.19; 606/204.45

(58) Field of Classification Search
USPC ............... 128/858; 606/199, 204.45; 2/15, 2/428–431, 434, 438, 440
See application file for complete search history.

(56) References Cited

U.S. PATENT DOCUMENTS

| | | | |
|---|---|---|---|
| 3,878,838 A * | 4/1975 | Lunn | ............................ 601/71 |
| 5,476,091 A | 12/1995 | Johnson | |
| 5,961,537 A | 10/1999 | Gould | |
| 6,332,465 B1 * | 12/2001 | Xue et al. | ................ 128/207.11 |
| 7,096,867 B2 * | 8/2006 | Smith et al. | ............. 128/207.11 |
| 8,051,850 B2 * | 11/2011 | Kwok et al. | ............. 128/200.24 |
| 2002/0138891 A1 * | 10/2002 | Spiteri | .............................. 2/15 |
| 2003/0079266 A1 * | 5/2003 | Magidson | ........................ 2/15 |
| 2008/0078414 A1 * | 4/2008 | Demas | ........................ 128/857 |
| 2010/0263673 A1 * | 10/2010 | Kielow et al. | ........... 128/206.15 |

* cited by examiner

*Primary Examiner* — Rachel Young
(74) *Attorney, Agent, or Firm* — F. Rhett Brockington

(57) ABSTRACT

The invention is an apparatus that blocks out light and improves breathing. The apparatus includes a sleep mask with an integral nasal dilation system. The nasal dilation system includes a nasal element mounted with on the nose section of the mask, where the nasal element in one version has a channel through which a band can move substantially orthogonal to the wearer's nose. Sidewalls center the band, and inward folded cuffs retain the band. The band encircles the wearer's head between the mask straps. It is threaded through the slideway and can slide therein equalizing side-to-side forces. The band is elastic and when stretched it generates an opposing force. Pressure is exerted on the nose by using the band in a stretched state. The extended band creates pressure on the slideway, which causes the nose section to press against the nostrils causing them to distend, which in turn dilates the nasal passages, and breathing is improved.

15 Claims, 4 Drawing Sheets

DILATED NASAL SLEEP MASK

BACKGROUND OF THE INVENTION

1) Field of the Invention

The invention relates generally to sleep masks, and more particularly to a sleep mask that has improved breathing.

2) Prior Art and Statement of the Problem

Sleeping is difficult for people who are easily awakened by light, as periodically light will be generated either from passing lights, for instance from a car, a train or a truck; and lights that illuminate when motion is detected. Light stimulates people's primeval instinct to awaken, as it is a normal reaction to awaken at first light. Inventions have artificially expanded the length of useable daylight, so that now people are awake during times they normally would be asleep, and people have a need to adjust their schedules so that they can continue to get to sleep, even in the presence of light. One approach has been to create window treatments that essentially block out all ambient light. Another approach is to use sleep masks. Sleep masks cover your eyes and block out most light, but generally not all light.

Another invention that can affect sleep is high speed travel, for instance in a jet airliner, where one can move from one time zone to another in a relatively short period of time. If the traveler is flying from East to West (i.e., NY to CA), the rate of travel is so fast that the day will be extended several hours, so that when the traveler arrives at his destination the traveler's body is saying it is eleven o'clock PM, but the current time at his destination is eight o'clock PM Pacific Standard time. For most travelers air flight from West to East is even more difficult. The time zone change from NY to Pairs is six hours. If your plane departs at six PM and you arrive in Paris five hours later, your body will think it is eleven o'clock, but actual Pairs time will be five o'clock AM. By the time the traveler gets in bed at midnight, it is sunrise in Paris. The exhausted traveler may only be able to get to sleep if he has a sleep mask to keep out the ambient light.

Sleep can also be disrupted when breathing is difficult, for instance by a deviated septum or in general by narrowed nasal passages. In U.S. Pat. No. 5,476,091 to Bruce C. Johnson some of the symptoms and causes are discussed. Humans are often subject to interior obstruction of their nasal passages which makes breathing more difficult. Examples of such obstruction are a deviated septum typically resulting from injury to the nose, swelling of interior nose tissues due to allergic reactions, and the nasal symptoms present in those suffering with the common cold. The morphology of the lower portion of a nostril, immediately interior the entrance to the nostril, is the vestibule. The vestibule tapers inwardly to a narrowed neck-like area called the nasal valve. Nasal passages, posterior to the nasal valve, widen again. Nasal obstructions commonly occur at the nasal valve to the point that the nasal valve may be substantially blocked. Commonly, the lateral wall (i.e., the outer wall tissues of the nasal passage) at the nasal valve is loose with the result that the outer wall tissues are draw-in during the inhalation portion of the breathing process, and this can substantially or completely block passage of air through the nasal passage. Blockage of the nasal passage is compensated by sustained mouth breathing, which over a long period of time may cause lung irritation due to the inhalation of foreign particles that would otherwise be filtered if the breath had passed through the nose. Nasal blockages lead to sleep disturbances, sleep irregularities, snoring or a combination thereof. Additionally, a person with such a condition may wake often, probably because that person is not easily inhaling sufficient quantities of oxygen.

Some solutions include medications (nasal sprays), surgery, and mechanical aids termed nasal dilators. Mechanical aids have been used in attempts to open nasal passages. Such dilators have been both of the internal variety which in effect push out the sides of the nasal passages to open them, and of the external variety effectively pulling on the sides of the nasal passages to open them. The internal types require insertion in the nasal passages, Johnson in U.S. Pat. No. 5,476,091 discloses an external variety dilator formed with a base material resilient strip having an adhesive layer that is adhered to the exterior surface of the nose. A version of the strip is sold under the trade name of Breath Right Strip™.

SUMMARY OF THE INVENTION

The invention is an apparatus that is a sleep mask with an integral nasal dilation system. The invention simultaneously addresses two issues that keep people awake. The invention blocks out light and it improves their breathing by dilating their nostrils (i.e., external nares). Dilation is accomplished without the use of adhesive strips. The adhesive on the strips over the course of a period of sleep, can be weakened causing the resilient strip to fail, or at best leave a sticky adhesive residue when the strip is removed. Perspiration, facial lotions and natural skin oils all interfere with adhesion, but have no effect on the disclosed invention. As will be seen, an aspect of the invention is that the nasal dilation system can optionally be partially disconnected from the sleep mask, so that if the user is not having breathing problems, then the invention can be used as a conventional sleep mask.

The sleep mask has a nose section, where a medial portion of the mask projects outward providing a contoured area that conforms to a bridge of the user's nose. The nose section substantially rests on the nose, therein providing partial support and self-centering for the mask. The nose section has a zone perimeter barrier that seals out light. In one aspect of the invention the sleep mask has a pair of ocular sections, wherein each of the ocular sections covers an eye and can be substantially convex in shape, therein providing sufficient clearance that a user's eye lashes do not brush against the mask when the user opens or closes his eyes. The nasal dilation system includes a nasal element, which in one variation is a slideway element, mounted on the outside of the nose section of the mask, and a band in contact with the nasal element. When the nasal element is a slideway element the band typically is threaded through the slideway element, where the band can smove through the slideway. The band has at least a portion that is elastic, and when stretched the band generates an opposing force in terms of a pressure. The pressure generated by a stretched band is applied to the nasal element, which in turn produces a pressure onto the nose section, which in turn applies the pressure onto the user's nose causing the nostrils to distend.

In the particular case when the nasal element is a slideway element, the slideway element permits the band to slide substantially orthogonally over the nose, where the slideway element functions substantially as a sleeve for guiding the band. It is another aspect of the invention that slideway element is at least partially open or can be opened so that the band can be removed from the slideway element and a different band can be positioned in the slideway element. Furthermore, the band can be easily extended so that it can be slipped on or off a user's head. The slideway element can also accept more than one band if the user wishes to build up pressure incrementally. The band can be continuous so that no adjustment to shorten or lengthen it is required, where the level of pressure is a function of the physical and parametric properties of the band. For instance, physical properties are thickness and elongation and parametric properties are the orientation of the elastomer. Within a group of elastomers, for instance a polyurethane elastomer, the band suitable for a user can be selected from a recommended modulus or selected by the user through trial an error.

Pressure exerted on the nose using the nasal dilator can also manifest itself by creating some pressure near the end the nose. The pressure causes the nostrils to distend, which in turn dilates the nasal passages. A small amount of dilation produces a significant improvement in breathing. The passages are normally relatively narrow, and the dilation makes them rounder, and rounder passages have much more square, area. For instance, an oval passage that is 2 mm long and 0.5 mm wide has a perimeter of ~9.16 mm and an area of 3.14 mm$^2$. If the passage is widened to 0.6 mm the area increases to 3.71 mm$^2$, which is about an 18% increase in area.

In most cases only a very small dilation is sufficient to improve sleep. An advantage of a continuous band is that there is minimization of entanglement of the user's hair in the band, and selected bands will have a known modulus. The band also functions to hold edges of the sleep mask close to the user's skin, which improves the effectiveness of the mask at blocking out light. A significant advantage of the invention is that it eliminates the need for the use of adhesive strips, and therefore the accompanying concern with their use including allergic skin reactions to the adhesive, removal of the strip, and cleaning off residual adhesive.

BRIEF DESCRIPTION OF THE DRAWINGS

The foregoing and other objects will become readily apparent by referring to the following detailed description and the appended drawings in which.

DETAILED DESCRIPTION

Figure 1:
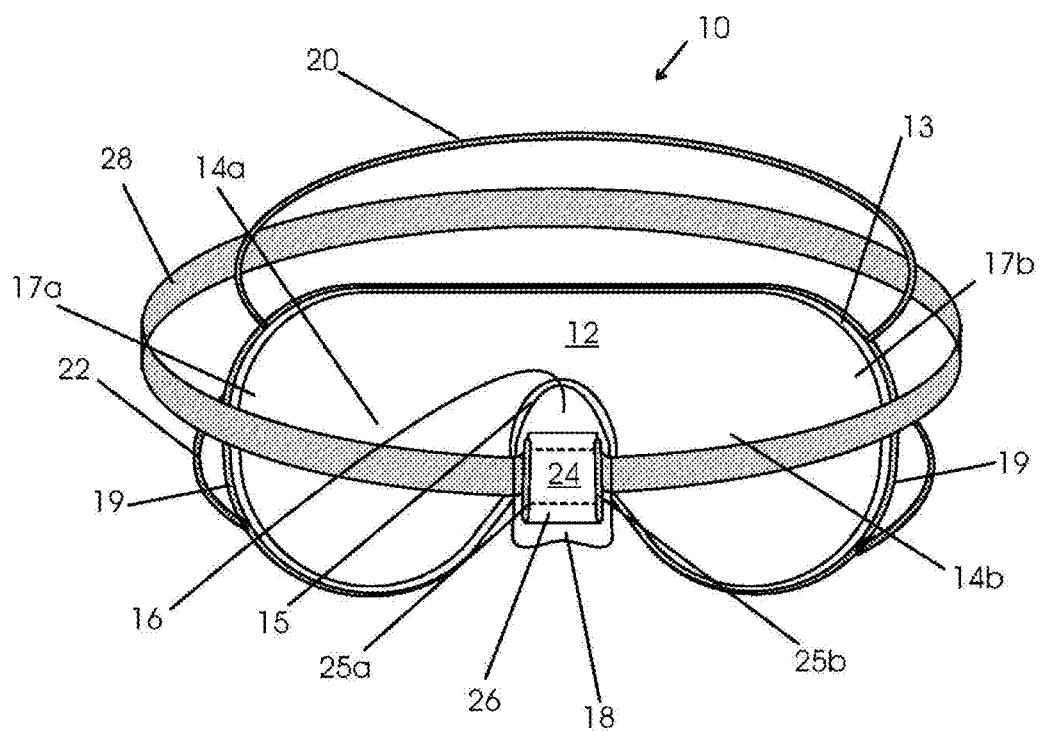
FIG. 1 is an illustration of an embodiment of the invention, a sleep mask with an integral nasal dilation system.

The invention 10 is an apparatus that is a sleep mask with an integral nasal dilation system. An embodiment of the invention is shown in FIG. 1. The sleep mask 12 is composed of a pair of ocular sections (14a—right eye, 14b—left eye), that cover the wearer's eyes, and a nose section 16 having an inside (not visible) and an outside that covers a front portion of the wearer's nose. The nose section has a zone perimeter barrier 15 that seals out light. The mask 12 also has a seal zone 19 composed of a material that contours to the wearer's face to occlude light and a perimeter element 13 that defines and supports the edges of the mask 12. The mask has an upper tensioning element 20 and a lower tensioning element 22 that taken together provide enough tension to keep a right side 17a and a left side 17b of the mask in contact with the wearer's face. The tensioning elements are attached to the sides of the perimeter element 13 of the mask proximate to seal zone 19. In the illustrated embodiment the tensioning elements are elastic straps, and can easily be stretched around the wearer's head. In other embodiments, the tensioning elements can be adjustable, for instance with a small clasp or bead. Additional support and positioning of the mask is provided by the nose section 16, which follows and rests on the medial contours of the front of the wearer's nose. The mask is preferably composed of a substantially opaque material, however, this can be tailored to meet the wearer's desires as to the degree of transparency.

The nasal dilation system is composed of a nasal element 24 (e.g., slideway element) mounted on the bridge portion 18 of the nose section 16 of the sleep mask 10. In the illustrated version the slideway element 24 optionally has a covering element 26 that snaps onto the slideway element 24. The nasal dilation system has a continuous elastic band 28 that encircles the wearer's head and is threaded through the slideway element. Where it passes through the slideway element, the band 28 is shown in ghost as a dashed line. The band can move through the slideway element 24, so that it is self adjusting, therein equalizing any side-to-side force so that the net side-to-side vectors are zero. Note, that the position of the band is between the upper tensioning element 20 and the lower tensioning element 22, and there is no tendency to move up or down on the wearer's head. The elastic hand contacts the sides 17a,17b of the mask 12, therein holding the edge seal zone 15 adjacent to the perimeter 13 of the sleep mask 12 against the user's skin. The band therein also improves the effectiveness of the mask at blocking out light. The dimensions and composition of the band are selected to slightly depress the nose, which is substantially composed of cartilage, wherein upon compression the nostrils distent therein enlarging the nasal passages. Pressure is exerted on the nose by using the band in a slightly stretched state. The extended band creates downward force of the nasal element, which as illustrated is a slideway, which causes the nostrils to distend, which in turn dilates the nasal passages. A small amount of dilation produces a significant improvement in breathing. Nasal passages are normally relatively narrow, and the dilation makes them rounder, and rounder passages allow air to move through them with less restriction. Breathing is improved.

Figure 2:
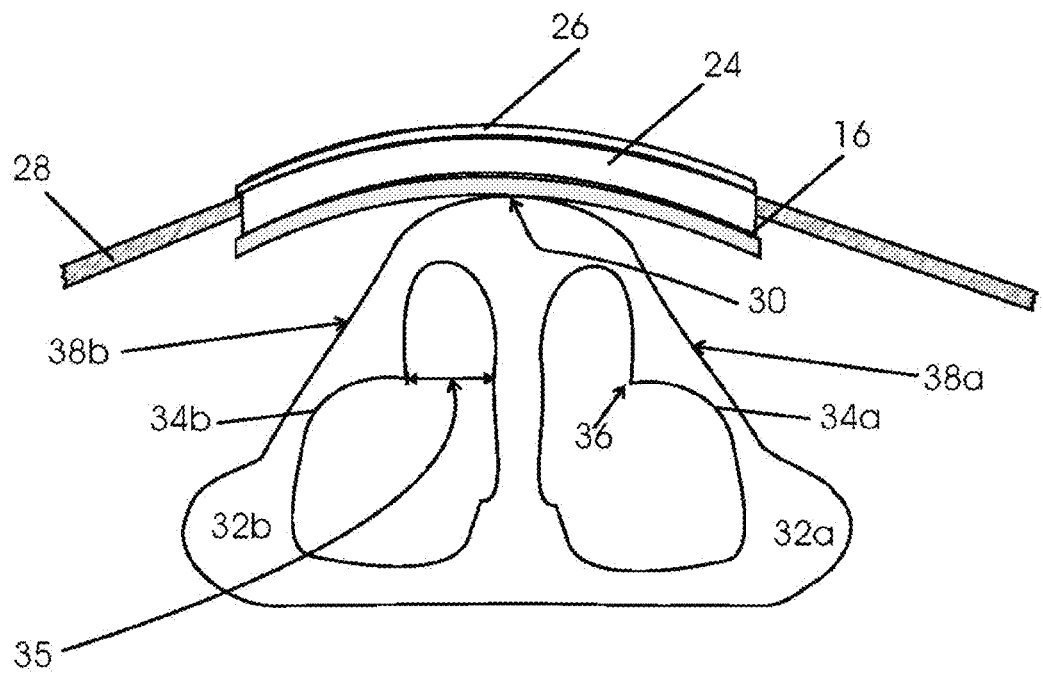
FIG. 2 is a view of the nostrils of the nose looking into the nasal passages, wherein no pressure is applied on the nose by the nasal dilation system, and also illustrating that the most ventral portions of the passages are relatively narrow.
Figure 3:
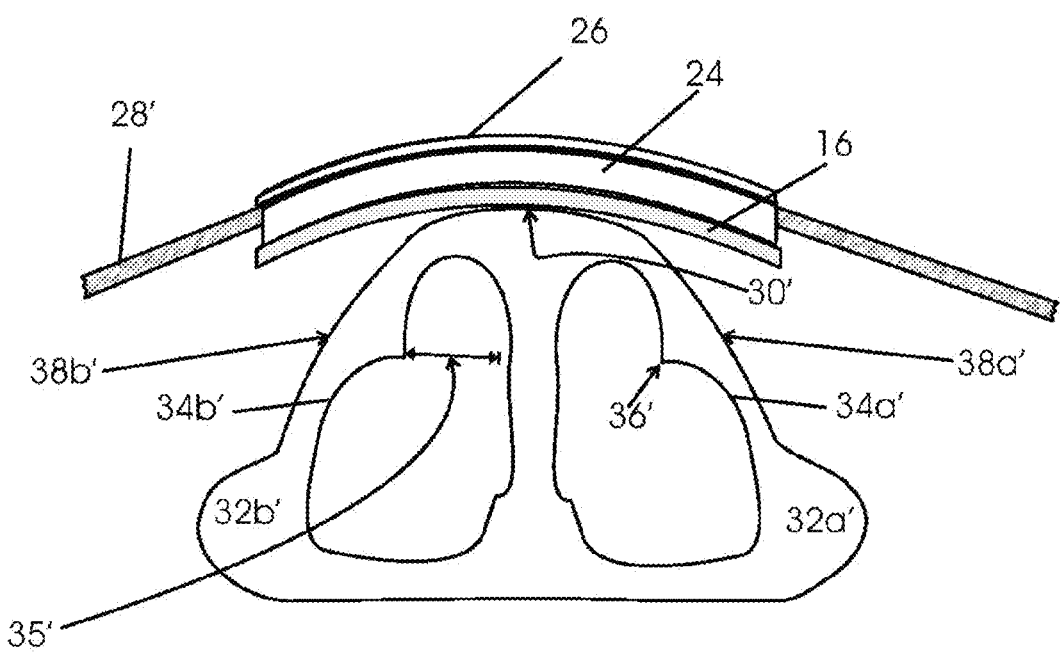
FIG. 3 is a view of the nostril of the nose looking into the nasal passages, wherein pressure is be applied on the nose by the nasal dilation system, illustrating that the most ventral portions of the passages have rounded, this in effect causing dilation and improved breathing.

FIG. 2 is a view of the nostrils (external nares) 32a, 32b and nasal passages 34a, 34b in the vestibule, before the nasal dilation system is applying any pressure, and in FIG. 3 the same view when pressure is applied by the nasal dilation system. The band 28 is not extended. The slideway element 24 is mounted to the nose section 16 of the mask. The band 28 is threaded through the slideway element 24, shown here with a cover element 26. Essentially, no pressure is being applied to the front of the nose 30, as shown by the curvature. The right and left side walls 38a,38b of the right and left nostrils 32a, 32b are substantially straight. The right and left nasal passages 34a, 34b are relatively narrow, especially toward the front (ventral side). This is shown by the arrow, which schematically illustrates the radius 35 of the left passage 34b.

FIG. 3 illustrates the effect when the band is slightly extended to create pressure on the slideway element 24. For clarification, in FIG. 3 only, an indicia having an apostrophe indicates that there has been a deformation due to the pressure. The pressure has caused a slight deformation of front of the nose 30', such that the curvature is reduced. The curvature spreads to the right and left side walls 38a,38b of the right and left nostrils 32a, 32b, which now are very slightly curved, as they are being pushed outward by the pressure. In turn, the right and left nasal passages 34a, 34b are slightly dilated, especially the narrower nasal passages. This is illustrated by the radius 35'. The length of the original line 35 is shorter than the distance of radius 35'. The cusp 36 in FIG. 2, which delineates the narrower portion of the nasal passage from the wider portion of the nasal passage, is slightly shifted as shown in 36' of FIG. 3, suggesting that the wider portion of the nasal passage may also be opened up. The greater the dilation, the less restriction to breathing through the nose, and the less breathing required by mouth. Breathing through the nose is preferred over breathing through the mouth because the nose is much more effective at humidifying and catching particulates in the inhaled air. The better the air quality, the less wear and tear on your lungs. Also, the less breathing through your mouth, the less snoring, which has its own set of ramifications.

Figure 4:
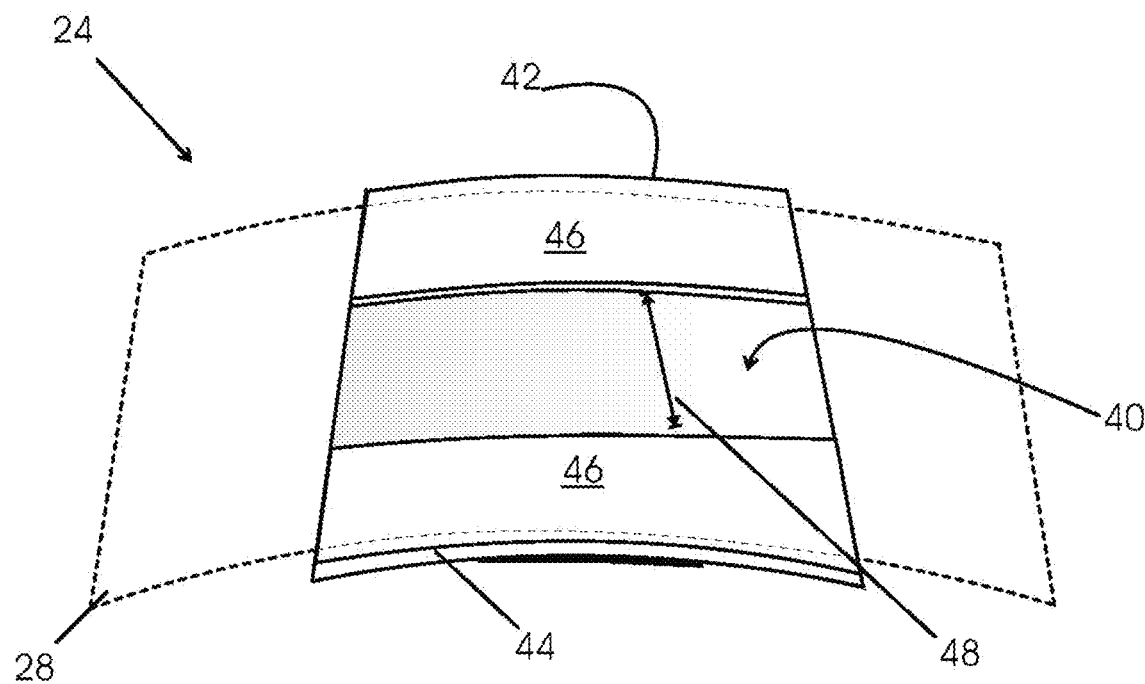
FIG. 4 is a frontal view of the nasal element that is a slideway element without a cover that illustrates that the slideway element is similar to a flattened slotted short sleeve that includes a channel through which the band can move, sidewalls that hold the band in the channel and a pair of inward folded cuffs that retain the band, where the inward folded cuffs also provide the slot for the band to be positioned in the slideway element, wherein the band is positioned by pinching the side edges of the band so that it folds over and the edges of the band can be pushed into the slideway element.

FIG. 4 is a frontal view of the slideway element 24. In this view there is no cover element. In this embodiment the slideway element 24 is similar to a flattened slotted short sleeve, where the slideway element includes a channel 40 through which the band can move, an upper sidewall 42, a lower sidewall 44 where the sidewalls centers the band 28 in the channel 40. There is also a pair of inward folded cuffs 46 that retain the band 28. The slot 48 formed by the inward folded cuffs 46 also provides an access point for positioning the band in the slideway element 24, wherein the band 28 is positioned by pinching the side edges of the band so that it folds over and the edges of the band can then be pushed into the slideway element.

Figure 5:
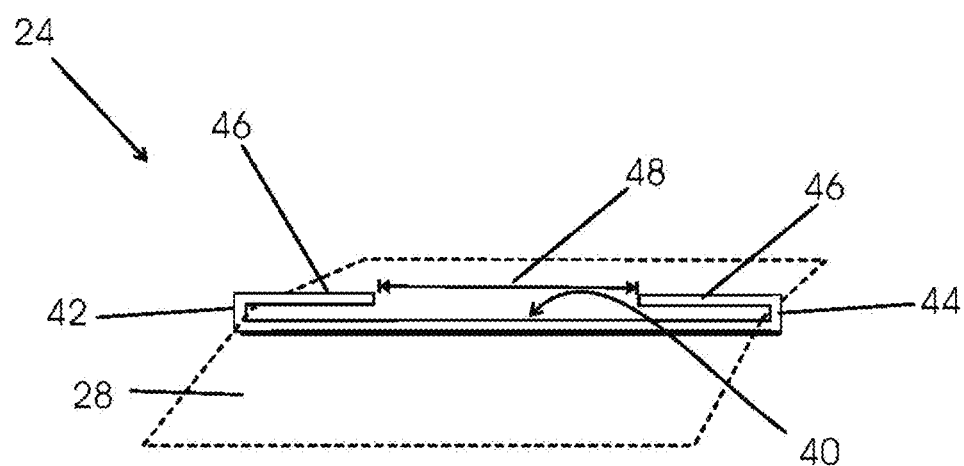
FIG. 5 is an end of the slideway element.

FIG. 5 is a side view of the slideway element. The band enters and exits the slideway element approximately orthogonal to a center line for the nose.

Figure 6:
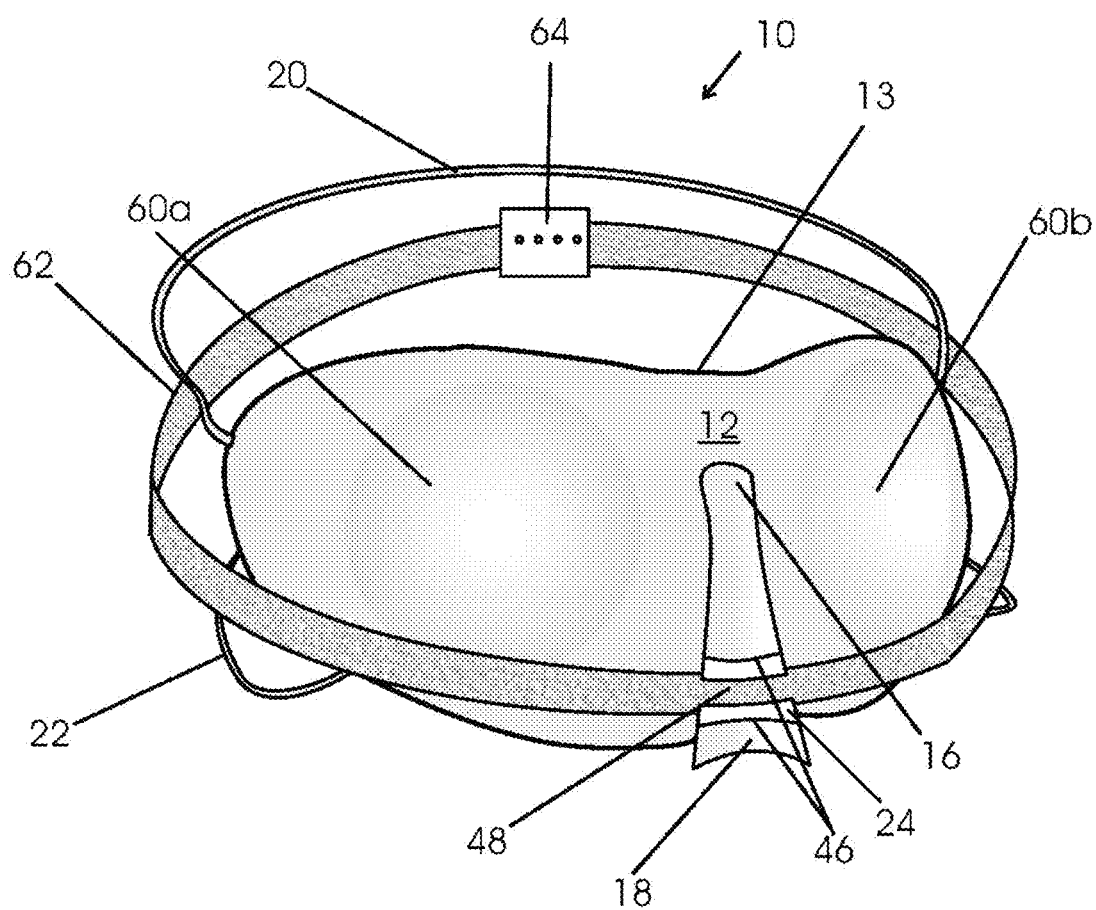
FIG. 6 is an alternate embodiment end of the slideway element, where the mask has a pair of supraocular sections, that allow the wearer to blink without their eyelashes contacting with the sleep mask.

FIG. 6 is another embodiment of the invention 10 wherein the sleep mask 12 is composed of a pair of supraocular sections (60a—right eye, 60b—left eye), that cover the wearer's eyes, and a contiguous nose section 16 that covers a front portion of the wearer's nose. Each of the supraocular sections covers an eye and is substantially convex in shape, therein providing enough clearance that a user's eye lashes do not brush against the mask when the user opens or closes his eyes. The mask has an upper tensioning element 20 and a lower tensioning element 22 that taken together provide enough tension to keep sides of the mask in contact with the wearer's face. The tensioning elements are attached to the sides of the perimeter element 13. In the illustrated embodiment the tensioning elements are elastic straps, and can easily be stretched around the wearer's head. In other embodiments, the tensioning elements can be adjustable, for instance with a small clasp or bead. Additional support and positioning of the mask is provided by the contiguous nose section 16, which follows and rests on the medial contours of the front of the wearer's nose. The mask is preferably composed of a totally opaque material.

The nasal dilation system is composed of a nasal slideway element 24 mounted on the bridge portion 18 of the nose section 16 of the sleep mask 10. In the illustrated version the slideway element 24 has no covering element 26, and you can see a portion of the band through the slot 48 and the cuffs 46. The band can be removed from the slideway element thereby disconnecting the nasal dilation system from the sleep mask. If the user is not having breathing problems, then the invention can be used as conventional sleep mask. In the illustrated embodiment the band is an adjustable elastic band 62 with an adjusting component 64 that is substantially not elastic. The band can move through the slideway element 24, so that it is self-adjusting, therein equalizing any side-to-side force so that the net side-to-side vectors are zero. Note, that the position of the band is between the upper tensioning element 20 and the lower tensioning element 22, and there is no tendency to move up or down on the wearer's head. The elastic band contacts the sides of the mask 12, therein holding the perimeter 13 of the sleep mask 12 against the user's skin. The band therein also improves the effectiveness of the mask at blocking out light. The dimensions and composition of the band are selected to slightly depress the nose, which is substantially composed of cartilage, wherein upon compression the nostrils extend therein enlarging the nasal passages. Pressure is exerted on the nose by using the band in a slightly stretched state. The extended band creates downward force of the slideway element, which causes the nostrils to distend, which in turn dilates the nasal passages. A small amount of dilation produces a significant improvement in breathing. Nasal passages are normally relatively narrow, and the dilation makes them rounder, and rounder passages allow air to move through them with less restriction. Breathing is improved.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim is expressed as a means or step for performing a specified function, it is intended that such claim be construed to cover the corresponding structure, material, or acts described in the specification and equivalents thereof, including both structural equivalents and equivalent structures.

What is claimed is:

1. An apparatus that can make sleeping easier for a wearer by blocking out light and dilating one or more nasal passages of the wearer, wherein said apparatus comprises:
   a) a sleep mask comprising:
      i) a pair of ocular sections composed of an opaque material, wherein each ocular section has a portion that is adapted to cover a wearer's eye;
      ii) a nose section that is adapted to cover a front portion of the wearer's nose, wherein the nose section, which extends from a bridge of the mask, is elongate and angled projecting outward from the mask providing a contoured open-ended covering;
      iii) a perimeter element that provides dimensional stability and support to an edge of the mask, minimizing the mask from distorting when it is under tension;
      iv) a left side and a right side that are contiguous with the pair of ocular sections;
      v) an upper tensioning strap attached to an upper perimeter edge of the left side and the right side, where said upper strap is adapted to stretch around the wearer's head;
      vi) a lower tensioning strap attached to a lower perimeter edge of the left side and the right side, where said lower strap is adapted to stretch around the wearer's head;

b) an integral nasal dilation device comprising:
  i) a nasal slideway element mounted about orthogonal on the front of said nose section, where said slideway element has an arched channel that lengthwise is orthogonal to a medial line of the wearer's nose, an upper sidewall, a lower sidewall, and a pair of inward folded cuffs that provide limited access to the channel of the slideway element; and
  ii) a band, which is a continuous loop, that is positioned and adapted to encircle the wearer's head between the upper and lower strap, where said band is threaded through the slideway element, such that the band can slide through the slideway therein equalizing any side-to-side force, wherein said band has at least a portion that is elastic, such that when it is stretched the band generates an opposing force, and a pressure is adapted to be exerted on the nose by using the band in a stretched state, therein improving breathing.

2. The apparatus according to claim 1, wherein the band is adapted to have minimal entanglement with a wearer's hair.

3. The apparatus according to claim 1, wherein the band has a standardized modulus, such that the amount of pressure generated by the stretched band is known.

4. The apparatus according to claim 1, wherein the band is adapted to hold edges of the sleep mask close to the user's skin, which improves the effectiveness of the mask at blocking out light.

5. The apparatus according to claim 1, wherein the integral nasal dilation device eliminates the need for the use of adhesive strips, and therefore the accompanying concern with their use including allergic skin reactions to the adhesive, removal of the strip, and cleaning off residual adhesive.

6. The apparatus according to claim 1, further comprising a cover element for the slideway element, wherein the cover element is decorative and functional, covering the pair of inward folded cuffs of the slotted cover and keeping the channel free of obstructions.

7. The apparatus according to claim 1, wherein the band can be removed, and the apparatus can function as a conventional sleep mask.

8. An apparatus that can make sleeping easier for a wearer by blocking out light and dilating one or more nasal passages of the wearer, wherein said apparatus comprises:
  a) a sleep mask comprising:
    i) a pair of supraocular sections, where each supraocular section cover is adapted to cover a wearer's eye, wherein the supraocular sections are convex in shape and are adapted to provide enough space for the wearer to blink without their eye lashes contacting the mask;
    ii) a nose section that is adapted to cover a front portion of the wearer's nose, where the nose section is continuous with the supraocular sections, wherein the nose section, which extends from a bridge, is elongate and angled to project outward from the mask providing a contoured covering;
    iii) a perimeter element that defines and supports edges of the mask;
    iv) a left side and a right side contiguous with the pair of supraocular sections;
    v) an upper tensioning strap attached to an upper perimeter edge of the left side and the right side, where said upper strap is adapted to stretch around the wearer's head;
    vi) a lower tensioning strap attached to a lower perimeter edge of the left side and the right side, where said lower strap is adapted to stretch around the wearer's head;
  b) an integral nasal dilation device comprising:
    i) a nasal slideway element mounted about orthogonal on the front of said nose section, where said slideway element has an arched channel that lengthwise is orthogonal to a medial line of the wearer's nose, an upper sidewall, a lower sidewall, and a pair of inward folded cuffs that provide limited access to the channel of the slideway element; and
    ii) a band, which is a continuous loop, that is positioned and adapted to encircle the wearer's head between the upper and lower strap, where said band is threaded through the slideway element, such that the band can slide through the slideway therein equalizing any side-to-side force, wherein said band has at least a portion that is elastic, such that when it is stretched the band generates an opposing force, and a pressure is adapted to be exerted on the nose by using the band in a stretched state, therein improving breathing.

9. The apparatus according to claim 8, wherein the band is adapted to have minimal entanglement with a wearer's hair.

10. The apparatus according to claim 8, wherein the band has a standardized modulus, such that the amount of pressure generated by the extended band is known.

11. The apparatus according to claim 8, wherein the band is adapted to hold edges of the sleep mask close to the user's skin, which improves the effectiveness of the mask at blocking out light.

12. The apparatus according to claim 8, wherein the integral nasal dilation device eliminates the need for the use of adhesive strips, and therefore the accompanying concern with their use including allergic skin reactions to the adhesive, removal of the strip, and cleaning off residual adhesive.

13. The apparatus according to claim 8, further comprising a cover element for the slideway element, wherein the cover element is decorative and functional, covering the pair of inward folded cuffs of the slotted cover and keeping the channel free of obstructions.

14. The apparatus according to claim 8, wherein the band can be removed, and the apparatus can function as a conventional sleep mask.

15. The apparatus according to claim 8, wherein the band is adjustable as to length, size, count, and modulus, so the pressure generated by the band in the stretched state can be adjusted.

* * * * *